United States Patent [19]
Abbott et al.

[11] Patent Number: 5,823,774
[45] Date of Patent: Oct. 20, 1998

[54] DYNAMICALLY SEALED SURGICAL DRILL

[75] Inventors: Dwight E. Abbott; Kenneth L. Brown, both of Redding, Calif.

[73] Assignee: Arthrotek, Inc., Warsaw, Ind.

[21] Appl. No.: 594,581

[22] Filed: Jan. 31, 1996

[51] Int. Cl.⁶ .................................................. A61C 1/02
[52] U.S. Cl. ...................... 433/115; 433/116; 606/180; 384/478; 277/133
[58] Field of Search .................... 433/115, 116, 433/120, 122, 126–129, 132; 606/80, 180; 384/135, 478; 277/13, 14 R, 25, 133

[56] References Cited

U.S. PATENT DOCUMENTS

| | | |
|---|---|---|
| 1,899,164 | 2/1933 | Raule . |
| 2,003,000 | 5/1935 | Kelps ........................................ 277/133 |
| 2,188,856 | 1/1940 | Chievitz ................................... 277/133 |
| 2,581,504 | 1/1952 | Wilfley et al. . |
| 2,622,845 | 12/1952 | Nickle et al. ............................ 277/133 |
| 2,983,519 | 5/1961 | Staunt . |
| 4,157,834 | 6/1979 | Burdette . |
| 4,202,102 | 5/1980 | Nakanishi . |
| 4,234,308 | 11/1980 | Leonard . |
| 4,292,027 | 9/1981 | Richmond . |
| 4,369,034 | 1/1983 | Garnier . |
| 4,890,941 | 1/1990 | Calafell, II et al. . |
| 4,975,056 | 12/1990 | Eibofner . |
| 4,992,023 | 2/1991 | Baker et al. . |
| 5,052,411 | 10/1991 | Schoolman . |
| 5,067,732 | 11/1991 | Szabo et al. . |
| 5,074,788 | 12/1991 | Nakanishi . |
| 5,078,601 | 1/1992 | Badoz et al. . |
| 5,167,501 | 12/1992 | Castellini . |
| 5,252,065 | 10/1993 | Nakanishi . |
| 5,423,678 | 6/1995 | Nakanishi . |
| 5,599,143 | 2/1997 | Düsing ..................................... 433/126 |
| 5,692,903 | 12/1997 | Nakanishi ............................... 483/115 |

FOREIGN PATENT DOCUMENTS

| | | |
|---|---|---|
| 2345985 | 2/1977 | France . |
| 998442 | 7/1965 | United Kingdom ................... 433/132 |

OTHER PUBLICATIONS

Jan. 1993 Walter Lorenz Surgical, Inc. Surgical Instrument Catalog, 5th Ed. Cover 2 p. 168, and Three Associated Drawings.

*Primary Examiner*—Ralph Lewis
*Attorney, Agent, or Firm*—Wooodard, Emhardt, Naughton Moriarty & McNett

[57] ABSTRACT

A device is disclosed that dynamically seals the collet of a high-speed surgical or dental drill from the ingress of contaminating substances with which the tool or collet of the drill comes into contact, such as blood, saliva, saline, tissue, bone chips, and tooth particles. The dynamic seal comprises an impeller and a bearing that rotatably supports both the impeller and a surgical tool; furthermore, the seal may be disposed within a burguard that is mounted on the distal end of a surgical drill. The spinning impeller has a disc portion that imparts a centrifugal force to the flow of contaminating substances and thereby pumps the flow entering through the tool opening radially outward through discharge holes in the burguard housing. The dynamic seal further includes an O-ring for sealing against the tool shaft and blocking the contaminating substances from continuing up the tool bore and into the collet of the surgical drill. A backring retains the O-ring in place.

37 Claims, 5 Drawing Sheets

DYNAMICALLY SEALED SURGICAL DRILL

FIELD OF THE INVENTION

The present invention relates to surgical drills and handpieces. More particularly, the present invention is directed to providing a surgical or dental drill having a collet that is dynamically sealed off from contaminating substances with which the tool or collet of the drill comes into contact during use, such as blood, saline, saliva, tissue, and bone or tooth particles.

BACKGROUND OF THE INVENTION

High speed surgical drills are used by dentists, oral-maxillofacial surgeons, and neurosurgeons to remove or grind teeth, notch bones, drill pilot holes for plates and screws, and sculpt bones. These high-speed drills, that is drills having angular velocities in the range of 25,000 revolutions per minute and above, are prone to fluid entering the drill during surgery. The spinning surfaces inside the drill create a negative pressure with respect to atmospheric pressure. This pressure differential sucks fluids such as blood, saliva, and saline and particles such as bone and tooth chips and into the tip of the drill during use. These fluids and particles contaminate the mechanics of the drill collet and cause corrosion, wear, or locking-up of the mechanisms. Eventually, the drill collet fails.

The obvious solution would seem to be to install a contact seal, such as an O-ring or ball seal, into the tip of the drill. However, because of the high speeds involved, contact seals cause too much friction and heat. Also, they quickly wear out. Therefore, contact seals are not an option in sealing high-speed drills.

Manufacturers of air-powered drill systems use positive air pressure to keep fluids out of the drill. The use of positive air pressure works well for air-powered systems because they have an air supply, but providing positive air pressure is difficult in an electrically powered system. Moreover, the air pressure inside an air drill creates a flow of air out the nose of the drill tip. This flow is of questionable sterility and could cause air embolisms if an air bubble were to enter an open vein.

Some manufacturers of high-speed surgical drills have implemented a handpiece spray by installing flushing ports in their drills and by providing a solvent-based flushing spray. The user is required to flush the drill with the spray after every surgery. The solvent spray may adequately remove contaminants; however, it does not extend the life of the drill because it removes the oils and greases that keep the collet mechanism running smoothly. A sprayed collet degrades during use and eventually has a mechanical failure due to the lack of lubricant. Also, the residual spray in the handpiece could dribble into the surgical site. In addition, spraying the handpiece after every surgery is expensive and time consuming for the user.

U.S. Pat. No. 5,074,788 to Nakanishi discloses a dental handpiece having one or more gap sections for preventing fine cut particles or chips of tooth from injuring the bearing of the handpiece. The gap sections extend in a generally axial direction between the tool opening and the front bearing of the handpiece located some distance proximal to the tool opening. In this known handpiece, the air pressure in the gap sections is such that the particles are drawn into one or more of the gaps and eventually expelled from the handpiece. Nakanishi does not disclose a dental handpiece for expelling fluids; further, the devices disclosed in U.S. Pat. No. 5,074,788 do not appear suited to sealing off the handpiece from fluid. Additionally, this device must be periodically dismantled in order to remove residual foreign matter from the gap sections.

SUMMARY OF THE INVENTION

The present invention as described in more extensive detail herein below obviates the disadvantages encountered in the prior art by providing a surgical or dental drill having a dynamic seal that prevents contaminating substances from being sucked into the collet of the drill. As used herein, contaminating substances denotes both fluid and particulate contaminants.

A principal object of the present invention is to provide a dynamic seal that counteracts the suction of the drill and reroutes the contaminants outside the drill, away from the internal collet mechanisms. The present invention is characterized by a device that rotates with the tool of the surgical drill and acts like a centrifugal pump to discharge the contaminants radially out of the drill.

Another object of the present invention is to provide a device that extends the life expectancy of a surgical drill by protecting its internal mechanisms yet requires minimum user maintenance.

In a preferred embodiment of the present invention, the dynamic seal is disposed within a burguard, a removable tool support, which is then attached to the distal end of a surgical drill. Additionally, a bearing disposed within the burguard rotatably supports the tool, as well as the dynamic seal. Furthermore, the dynamic seal comprises an impeller having a disc portion, whereby rotation of the impeller pumps contaminating substances in through the opening of the tool bore and out through discharge ports in the burguard, thereby preventing contamination of the mechanisms within the drill.

DESCRIPTION OF THE PREFERRED EMBODIMENT

Figure 1:
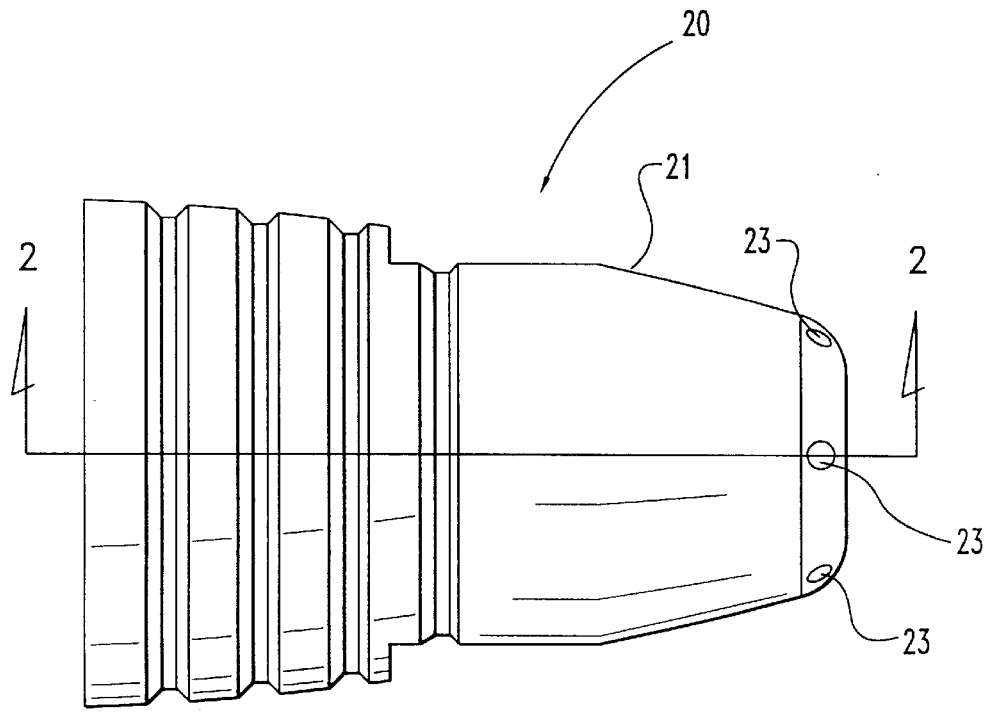
FIG. 1 is a side elevational view of a burguard.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
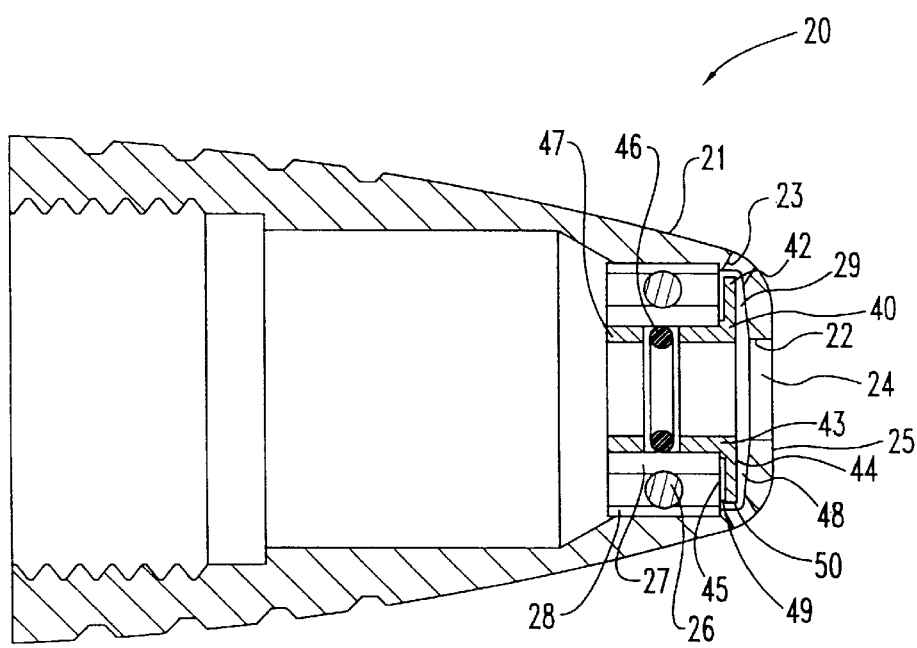
FIG. 2 is a sectional view of a medium-length burguard illustrating the dynamic sealing device of this invention.
Figure 6:
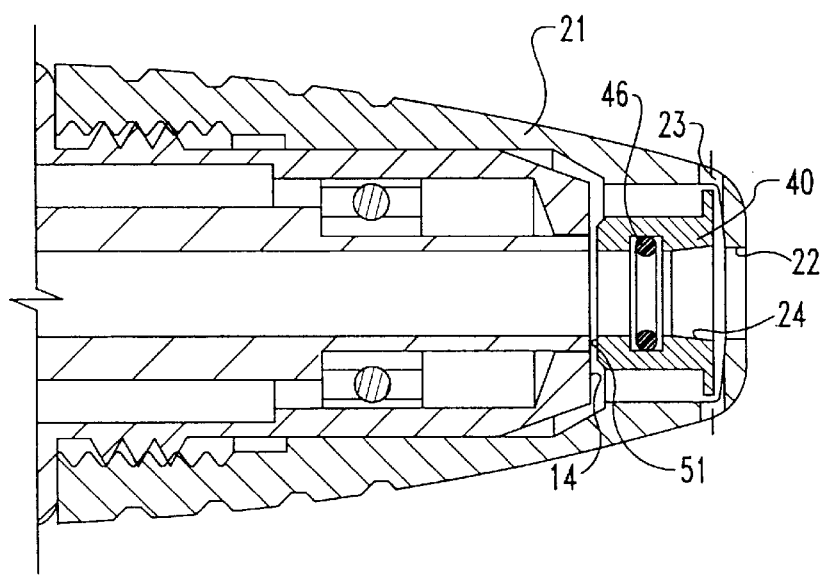
FIG. 6 is a sectional view of the distal portion of a collet and a medium-length burguard having straight discharge holes and a free-floating impeller.

Referring now to the drawings in detail, wherein identical numerals indicate the same elements throughout the figures, FIGS. 1 and 2 illustrate a medium-length burguard 20 that can be mounted onto a surgical drill. The burguard 20 comprises a housing 21, a shielded high-speed ball bearing 26 disposed within the housing 21, and a bore 24 extending through the burguard. As can be seen from FIGS. 3 and 4, the burguard bore 24 has a diameter sufficient to receive the shaft 16 of a surgical or dental tool 15. The burguard bearing 26 has an inner race 27 and an outer race 28 that is connected to the housing 21. Inner race 27 is free to rotate with a tool 15 that is rotatably driven by a motor (not shown) in the drill. Although other ball bearings are suitable for some applications, burguard bearing 26 is preferably designed for a dental drill and, more specifically, has a polyimide retainer, a non-toxic lubricant, and smooth surface finishes on the races. A suitable bearing is commercially available from New Hampshire Ball Bearing. Alternatively, the burguard 20 can contain no bearing at all as shown in FIG. 6, or can contain some other rotatable mounting means such as a bushing, journal bearing, magnetic bearing, or fluid bearing in place of the ball bearing.

The burguard housing 21 has a distal end 25, and the interior region of the housing between this distal end and the burguard bearing 26 constitutes a flow chamber 29. During operation of a surgical drill having an attached burguard 20, the rotation of tool 15 inserted into the drill creates a negative pressure with respect to atmospheric pressure at typical operating speeds e.g., 25,000 rpm to 75,000 rpm and higher. This pressure differential causes contaminating substances to be sucked into the burguard 20 through the tool opening 22 which is slightly greater than the tool shaft in order to provide clearance. The term "contaminating substances" encompasses both fluids such as blood, saline, and saliva as well as particulate matter such as tissue, bone chips, and tooth particles. After entering the flow chamber 29, the flow of contaminating substances encounters a rotatably mounted means for centrifugally pumping the flow out of the burguard through one or more discharge holes 23. In FIG. 2 the centrifugal pumping means is depicted as a centrifugal impeller 40 having a disc portion 42 that extends radially outward and a shoulder 43 that extends axially along the burguard bore 24. Furthermore, disc portion 42 projects radially into flow chamber 29 over substantially its entire diameter, and, consequently, impeller 40 has an outer diameter nearly as great as that of the burguard bearing 26. In the preferred embodiment, the bearing 26 has an inner diameter of about 0.125 in. and an outer diameter of about 0.25 in., the impeller 40 has a diameter about 0.225 in., and the disc portion 42 has a thickness about 0.015 in. Also, the thickness of the flow chamber 29 at the tool opening 22 is approximately the same as the thickness of the disc portion 42 of the impeller 40. However, these dimensions could be scaled or adjusted depending upon the application. Discharge holes 23 are positioned radially opposite impeller 40 and are aligned with the disc portion 42 of the impeller.

The disc portion 42 of the impeller 40 has a distal face 44 and a proximal face 45, either or both of which can be convex or concave; have ridges, vanes, or an otherwise patterned texture; or be smooth. The present invention operates well with smooth proximal and distal impeller faces; moreover, the use of smooth faces has the advantage of simplicity in machining. The distal face 44 of the impeller is spaced apart from the distal end 25 of the burguard housing 21, and the region of the flow chamber 29 defined therebetween is denoted a distal region 48. This distal region 48 extends from the burguard bore 24 substantially radially outward to the impeller edge 50 and is in flow communication with the discharge holes 23. Likewise, the proximal face 45 of the impeller is spaced apart from the burguard bearing 26, and the region of the flow chamber 29 defined therebetween is denoted a proximal region 49. This proximal region 49 extends substantially radially outward from the inner race 27 of the burguard bearing 26 to the impeller edge 50, and the proximal region 49 of the flow chamber 29 is also in flow communication with the discharge holes 23.

When contamination is sucked into the burguard 20 through the tool opening 22, it immediately impinges on the impeller 40 which rotates with the tool 15 during operation. Frictional engagement of the distal face of the spinning impeller 40 with the flow of contaminating substances causes the contaminating substances to begin spinning. The centrifugal force exerted on the flow due to its rotation induces the contaminating substances to traverse the distal region 48 of the flow chamber 29 radially outward. The magnitude of the centrifugal force exerted on the flow increases in the distal region 48 with radial distance from the tool opening 22 so that the flow is quickly flung past the impeller edge 50 and out the discharge holes 23. If some of the contamination does manage to round the impeller edge 50 toward the burguard bearing 26, it is urged, once again by centrifugal force, in the proximal region 49 radially outward to the discharge holes 23. That is, the proximal face 45 of the impeller 40 influences the movement of the flow in the proximal region 49 of the flow chamber 29 in the same way as the distal face 44 of the impeller acts on the flow in the distal region 48 of the flow chamber 29.

The impeller 40 is retained in the burguard 20 by pressing the impeller into the inner race 27 of the burguard bearing 26. A means for blocking the contaminating substances from continuing proximally up the burguard bore 24 along a tool shaft 16 inserted therein is provided in the form of an O-ring 46. The O-ring 46 seals against the outer diameter of the tool shaft 16 and is located radially inward of the inner race 27 of the burguard bearing 26. In addition, O-ring 46 is connected to the shoulder 43 of the impeller 40 so that when tool 15 is rotatably driven, the O-ring 46 and the impeller 40 rotate therewith. A backring 47 presses into the inner race 27 in order to retain the O-ring 46 in place.

Figure 5:
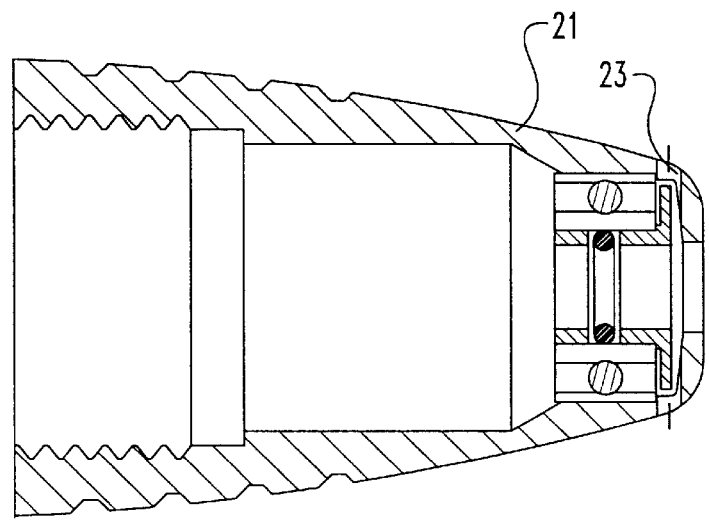
FIG. 5 is a sectional view of a medium-length burguard having straight discharge holes.

As seen in FIG. 1, the burguard housing 21 has discharge holes 23 around its circumference near the distal end 25 of the burguard. Discharge holes 23 need not necessarily be round; they could, for example, be square or slit-shaped. In the preferred embodiment, there are six discharge holes 23 having a diameter about 0.025 in.; however, the present invention can be practiced with a variety of hole sizes and quantities so long as the centrifugal pumping means has adequate back pressure to operate properly. Moreover, as illustrated in FIG. 2, the center of each hole 23 is aligned with the distal face 44 of the impeller 40. Also, the discharge holes 23 are preferably angled about 30° distal a line extending radially along the disc portion 42 of the impeller. This angle can also be measured with reference to the plane normal to the axis of rotation of the impeller. Although the present invention can be practiced with straight (i.e., non-angled) discharge holes, as illustrated in FIGS. 5 and 6, canting the discharge holes serves two purposes. The angled discharge holes 23 give the flow of contaminating substances an axial component and help direct the flow back down to the surgical site. Non-angled radial holes would cause the contaminating substances to be sprayed out over a larger area creating more of a mess. Also, the hole angle protects the proximal face 44 of the impeller 40 from outside fluid encroachment. If the holes are not angled, a backwash of fluid and particles alongside the burguard could more easily encroach upon the proximal face 44 of the impeller and cause the surgical drill to suck contaminating substances.

Figure 3:
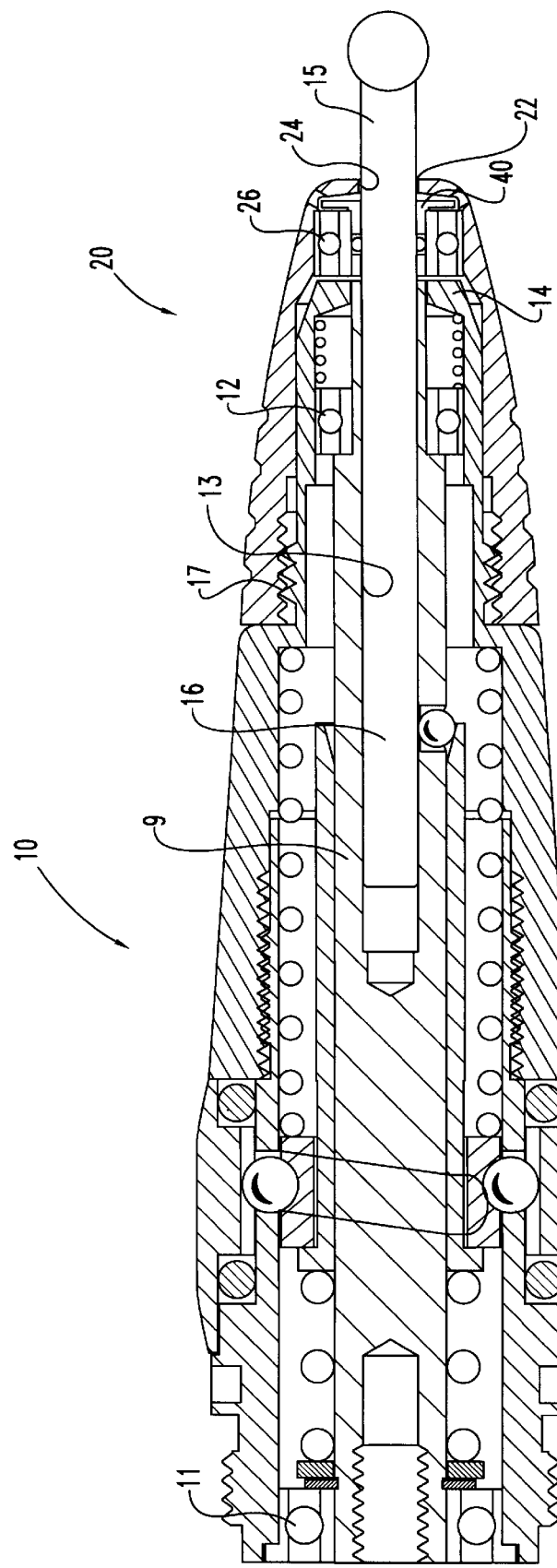
FIG. 3 is a sectional view of a surgical drill having a collet and a medium-length burguard attached thereto and having a tool inserted therein.
Figure 4:
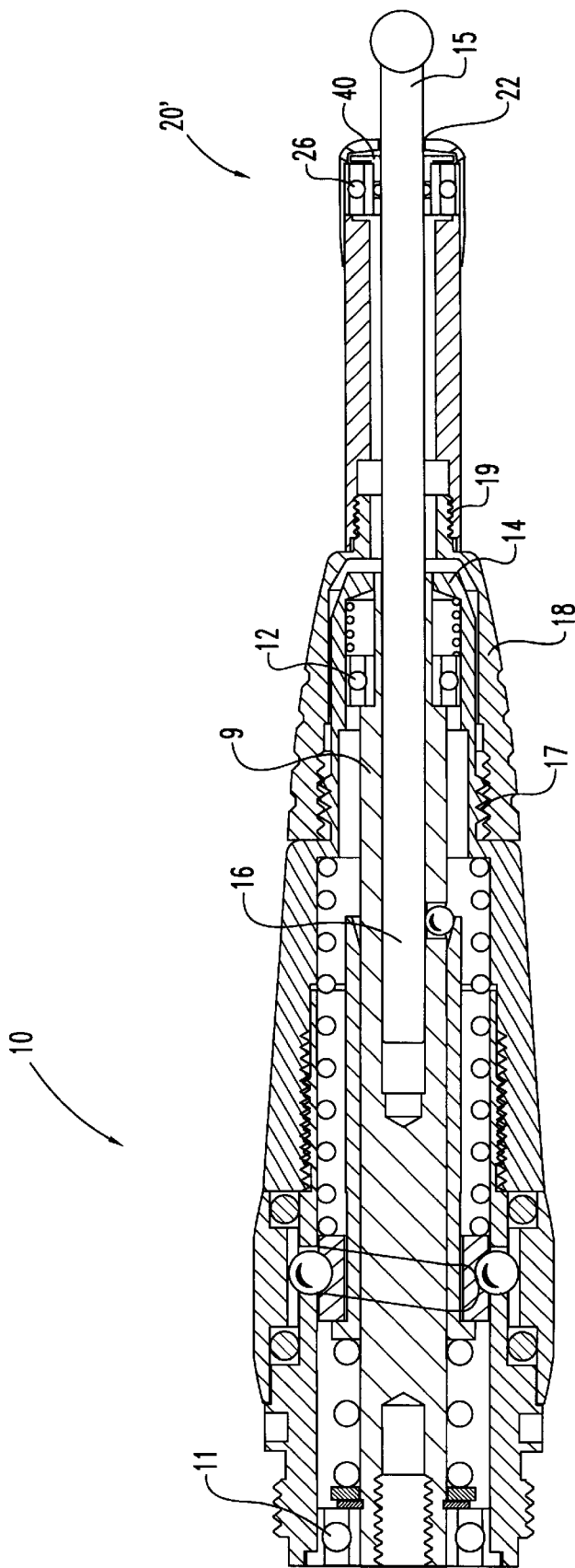
FIG. 4 is a sectional view of a surgical drill having a collet and a long burguard attached thereto and having a tool inserted therein.

FIGS. 3 and 4 show the orientations of burguards 20 and 20' of two different lengths connected to the collet of a surgical drill. A medium-length burguard 20 is preferably connected to the collet 10 by threads 17 as depicted in FIG. 3; however, other means of connection are contemplated. The collet 10 has a rear bearing 11, a front bearing 12, and a spindle 9 that is rotatably supported by the distal and proximal bearings. A suitable collet is commercially available, for example, Biomet's Lorenz MicroPower straight drill collet. A tool bore 13 extends into the collet 10 from the distal end 14 of the collet, and the tool bore 13 aligns with the burguard bore 24 such that, as a surgical or dental tool 15 is inserted into the surgical drill, the tool shaft 16 is received first by the burguard bore 24 and then by the tool bore 13. The spindle 9 is adapted for receiving and securing the tool 15 in the collet 10.

Illustrated in FIG. 4 is a long burguard 20' connected to an intermediate housing 18 that is in turn connected to the collet 10 of a surgical drill. The purpose of the intermediate housing 18 is to provide a means of connecting burguards of various lengths to the collet 10. Long burguards accommodate the long surgical or dental tools that extend the reach of the drill and enable the surgeon to access more remote sites. Despite the fact that the tool opening 22 is further removed from the internal collet mechanisms in a drill having a long burguard, the pressure differential created during operation of the drill can still cause the collet to suck contaminating substances. Hence, even the long burguard 20' requires a dynamic seal such as that provided by impeller 40 in order to protect the collet mechanisms from damage caused by the intrusion of fluid and particulate matter. As depicted in FIG. 4, the intermediate housing 18 is connected to the collet 10 and to the burguard 20' by threads 17 and threads 19, respectively.

FIGS. 5–8 illustrate alternative embodiments of the present invention. Discharge holes 23 need not necessarily be angled distally; instead they can extend directly radially through the burguard housing 21 as depicted in FIGS. 5 and 6. Also shown in FIG. 6 is a free-floating impeller 40. Instead of being rotatably supported by a bearing, the impeller 40 as well as the O-ring 46 ride on the tool which is, in turn, rotatably driven by the motor (not shown) of the drill. Since insertion of a tool would tend to push the proximal end 51 of the impeller 40 up against the distal end 14 of the collet 10, the proximal end 51 of the impeller 40 would be expected to experience some wear, but it would be limited by the tendency of the impeller 40 during rotation to center itself between the distal end 14 of the collet 10 and the distal end 25 of the burguard 20. Also, the burguard bore 24 is tapered near the tool opening 22 to facilitate entry of a tool into the free-floating slinger 40.

Figure 7:
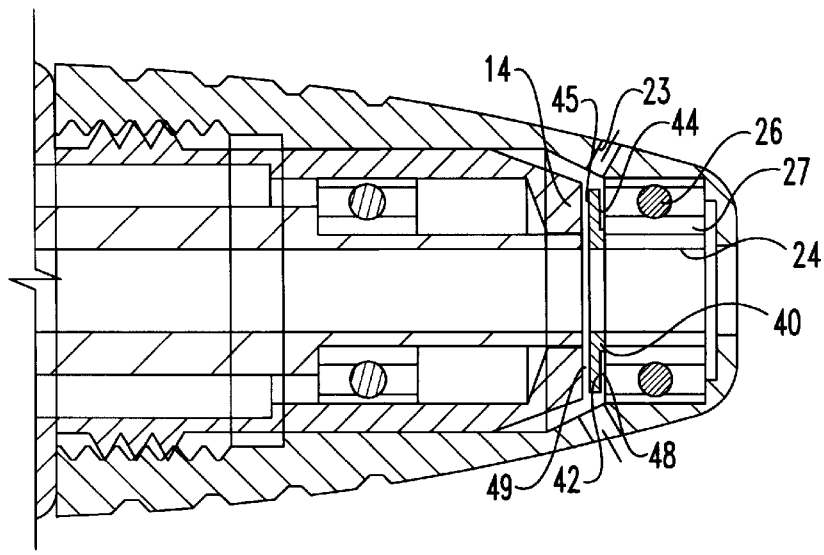
FIG. 7 is a sectional view of the distal portion of a collet and a medium-length burguard having an impeller mounted in the reverse orientation.
Figure 8:
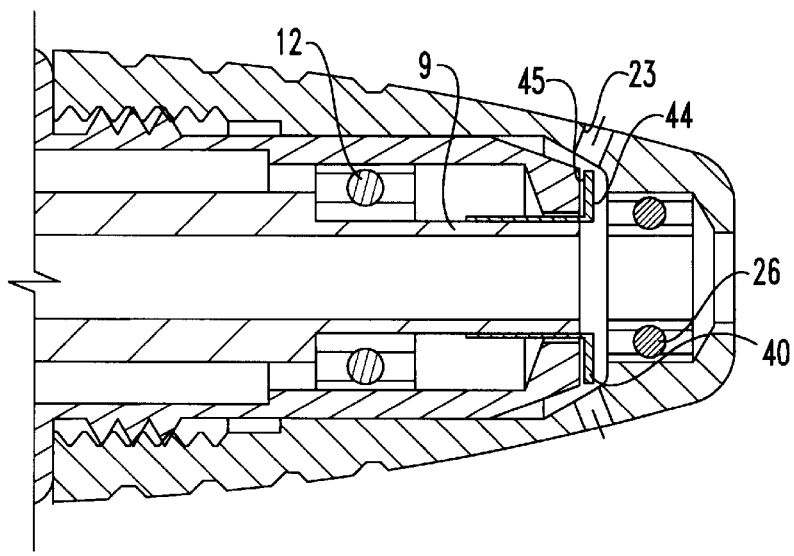
FIG. 8 is a sectional view of a medium-length burguard and distal portion of a collet having a spindle-mounted impeller.

FIGS. 7 and 8 show the impeller 40 located proximal to the burguard bearing 26. In the reverse orientation shown in FIG. 7, impeller 40 is connected to the inner race 27 of the burguard bearing 40, whereas it is connected to the spindle 9 of the collet 10 in FIG. 8. In the embodiment shown in FIG. 7, the proximal region 49 of the flow chamber 29, lying between the distal end 14 of the collet 10 and the proximal face 45 of the disc portion 42 of the impeller 40, extends substantially radially outward from the burguard bore 24 to the discharge holes 23. Also, the distal region 48 of the flow chamber 29 lies between the distal face 44 of the impeller 40 and the burguard bearing 26. In this reverse orientation, the proximal face 45 of the disc portion 42 of the impeller 40 aligns radially with the discharge holes 23. When the impeller 40 is connected to the spindle 9 of the collet 10 as in FIG. 8, the distal face 44 of the impeller 40 aligns radially with discharge holes 23. Also, in this spindle-mounted configuration, the impeller 40 is rotatably supported by the front bearing 12 of the collet 10, and the burguard bearing 26 acts solely to support a tool inserted into the drill.

Another alternative embodiment includes an impeller 40 formed integral with the tool shaft 16 and a tool opening 22 sized appropriately to allow passage therethrough of the tool shaft 16 with integral impeller 40.

While the invention has been described and illustrated in detail in the drawings and foregoing description, the same is to be considered as illustrative and not restrictive in character since only the preferred embodiment has been shown and described, and all changes and modifications that come within the spirit of the invention are desired to be protected.

What is claimed is:

1. A dynamic seal with integral impeller for removable attachment over the distal end of a surgical drill for preventing the ingress of contaminating substances into a bearing section of the drill, said dynamic seal comprising:

(a) a housing having a proximal end for removable placement on said distal end of said drill, a distal end with a tool opening therein, and at least one discharge hole in flow communication with said tool opening; and (b) a rotatably driven impeller located within said distal end of said housing adjacent said tool opening, said impeller being rotatably supported by said housing and removable therewith.

2. The apparatus of claim 1, wherein said rotatably driven impeller includes a disc portion.

3. The apparatus of claim 2, wherein said disc portion of said impeller has a smooth distal face.

4. The apparatus of claim 2, further comprising a bearing disposed within said housing and having an inner race and an outer race, said inner race being connected to said impeller.

5. The apparatus of claim 2, wherein said housing has at least one discharge hole aligned with said disc portion of said impeller for direct radial outlet of said contaminating substances out of said housing.

6. The apparatus of claim 5, wherein said housing comprises a plurality of discharge holes aligned with said disc portion and substantially equally spaced about the circumference of said housing.

7. The apparatus of claim 5, wherein said at least one discharge hole is angled about 30° distal a line extending radially along said disc portion of said impeller.

8. The apparatus of claim 5, wherein said housing comprises six discharge holes aligned with said disc portion and of a diameter of about 0.025 inches.

9. The seal of claim 1, further comprising a bearing disposed within said housing and having an inner race connected to said impeller and further having an outer race connected to said housing, wherein said impeller further includes a shoulder and flat distal and proximal faces, wherein said distal or proximal face is substantially radially aligned with said at least one discharge hole, wherein said housing further includes a bore therethrough, and wherein dynamic seal further comprises a means for blocking said contaminating substances from moving proximally up said bore and into said drill, said blocking means being connected to said shoulder of said impeller and located radially inward of said inner race of said bearing.

10. The dynamic seal of claim 1, further comprising a bearing directly supported by and within said distal end of said housing, wherein said impeller is directly supported by said bearing.

11. The dynamic seal of claim 10, wherein said housing includes a main housing portion and a distal extension threaded thereto.

12. A surgical drill handpiece, comprising:
   a collet having a spindle rotatably supported by a proximal bearing and a distal bearing, said spindle having a tool bore therein for receiving a tool shaft; and
   a dynamic seal on the distal end of said collet comprising a housing with a tool opening therein aligned axially with said tool bore, an impeller rotatably mounted within said housing and having a disc portion with a planar disc face, said disc face having a central tool opening therein with an inner edge which is immediately adjacent a tool shaft inserted in said spindle, and at least one discharge hole through said housing aligned radially with said planar disc face.

13. The apparatus of claim 12, wherein said disc portion has a planar distal face and a planar proximal face.

14. The apparatus of claim 13, wherein said distal face of said disc portion is spaced apart from said distal end of said housing and defines therewith a flow chamber extending substantially radially outward from said tool opening to said at least one discharge hole.

15. The apparatus of claim 13, wherein said housing further comprises a bore therethrough, and wherein said proximal face of said disc portion is spaced apart from said collet and defines therewith a flow chamber extending substantially radially outward from said bore to said at least one discharge hole.

16. The apparatus of claim 12, wherein said face of said impeller is smooth.

17. The apparatus of claim 12, wherein said housing comprises a plurality of discharge holes aligned radially with said planar disc face and substantially equally spaced about the circumference of said housing.

18. The apparatus of claim 12, wherein said at least one discharge hole is angled about 30° distal a line extending radially along said impeller.

19. The apparatus of claim 12, wherein said housing comprises six discharge holes aligned radially with said planar disc face and of a diameter of about 0.025 inches.

20. The surgical drill handpiece of claim 12, wherein said impeller is supported by said housing.

21. A surgical drill handpiece comprising:
   a collet having a spindle rotatably supported by a proximal bearing and a distal bearing, said spindle having a tool bore therein for receiving a tool shaft; and
   a dynamic seal on said distal end of said collet comprising a housing, a burguard bearing disposed within said housing, said burguard bearing having an outer race connected to said housing and having an inner race, and means for centrifugally pumping contaminating substances out of said housing.

22. The surgical drill handpiece of claim 21, wherein said centrifugal pumping means comprises a rotatably driven impeller having a disc portion.

23. The surgical drill handpiece of claim 22, wherein said disc portion of said impeller has a smooth distal face.

24. The surgical drill handpiece of claim 22, wherein said collet further comprises a tool bore, wherein said impeller further includes a shoulder, and wherein said housing includes a bore extending therethrough and aligned axially with said tool bore of said collet, and wherein said dynamic seal further comprises means for blocking said contaminating substances from moving proximally up said bore and said tool bore and into said collet, said blocking means being connected to said shoulder of said impeller and located radially inward of said inner race of said burguard bearing.

25. The surgical drill handpiece of claim 21, wherein said housing further includes at least one discharge hole radially aligned with said centrifugal pumping means for receiving said contaminating substances and communicating then out of said housing.

26. The surgical drill handpiece of claim 21, wherein said housing further comprises a plurality of discharge holes radially aligned with said centrifugal pumping means and substantially equally spaced about the circumference of said housing.

27. The surgical drill handpiece of claim 25, wherein said centrifugal pumping means has an axis of rotation, and said at least one discharge hole is angled about 30° distal a plane normal to said axis of rotation.

28. The surgical drill handpiece of claim 25, wherein said housing comprises six discharge holes radially aligned with said centrfugal pumping means and of a diameter of about 0.025 inches.

29. A surgical drill handpiece comprising:
   a collet having a spindle rotatably supported by a proximal bearing and a distal bearing, said spindle having a tool bore therein for receiving a tool shaft; and
   a dynamic seal on said distal end of said collet comprising a housing, a burguard bearing disposed within said housing, said burguard bearing having an outer race connected to said housing and having a rotatably driven inner race, and an impeller disposed within said housing and connected to said inner race.

30. The surgical drill handpiece of claim 29, wherein said impeller has a disc portion.

31. The surgical drill handpiece of claim 30, wherein said disc portion of said impeller has a smooth distal face.

32. The surgical drill handpiece of claim 29, wherein said collet further comprises a tool bore, wherein said impeller further includes a shoulder, and wherein said housing includes a burguard bore extending therethrough and aligned axially with said tool bore of said collet, and wherein said dynamic seal further comprises means for blocking contaminating substances from moving proximally up said burguard bore and said tool bore and into said collet, said blocking means being connected to said shoulder of said impeller and located radially inward of said inner race of said burguard bearing.

33. The surgical drill handpiece of claim 29, wherein said housing further includes at least one discharge hole radially aligned with said disc portion of said impeller.

34. The surgical drill handpiece of claim 33, wherein said housing further comprises a plurality of discharge holes radially aligned with said disc portion and substantially equally spaced about the circumference of said housing.

35. The surgical drill handpiece of claim 33, wherein said impeller has an axis of rotation, and said at least one discharge hole is angled about 30° distal a plane normal to said axis of rotation.

36. The surgical drill handpiece of claim 33, wherein said housing comprises six discharge holes radially aligned with said disc portion and of a diameter of about 0.025 inches.

37. A surgical drill handpiece, comprising:

a collet having a spindle rotatably supported by a proximal bearing arid a distal bearing, said spindle having a tool bore therein for receiving a tool shaft; and a dynamic seal on the distal end of said collet comprising a distal end enclosure with a tool opening therein aligned axially with said tool bore, at least one radial discharge hole through said enclosure, and an impeller disc rotatably mounted within said enclosure and having a central tool opening therein and a planar distal disc face, said distal face having an exposed planar surface extending along the entire radial span of said disc and radially aligned with said at least one discharge hole.

* * * * *

UNITED STATES PATENT AND TRADEMARK OFFICE
CERTIFICATE OF CORRECTION

PATENT NO. : 5,823,774

DATED : October 20, 1998

INVENTOR(S) : Dwight E. Abbott, et al.

It is certified that error appears in the above-identified patent and that said Letters Patent is hereby corrected as shown below:

Title page of the patent, under the prior art References Cited, please change "Kelps" to --Kelpe--.
Title page of the patent, under the prior art References Cited, please change "2,622,845" (Nickle et al. to --2,622,945--.
In column 7, line 1, please delete the word "said".
In column 8, line 14, please change "then" to --them--.
In column 8, line 16, please change "handpiece of claim 21" to --handpiece of claim 25--.
In column 9, line 3, please change "arid" to --and--.

Signed and Sealed this

Fifteenth Day of February, 2000

Attest:

Q. TODD DICKINSON

*Attesting Officer*  *Commissioner of Patents and Trademarks*